(12) United States Patent
Pimolsiriphol et al.

(10) Patent No.: US 10,807,942 B2
(45) Date of Patent: Oct. 20, 2020

(54) COALESCING AGENT DERIVED FROM SUCCINATE ESTER

(71) Applicant: PTT Global Chemical Public Company Limited, Bangkok (TH)

(72) Inventors: Vorapong Pimolsiriphol, Bangkok (TH); Yingrak Prai-in, Bangkok (TH); Thammarat Panyathanmaporn, Bangkok (TH)

(73) Assignee: PTT Global Chemical Public Company Limited, Bangkok (TH)

( * ) Notice: Subject to any disclaimer, the term of this patent is extended or adjusted under 35 U.S.C. 154(b) by 29 days.

(21) Appl. No.: 16/089,630

(22) PCT Filed: Mar. 29, 2017

(86) PCT No.: PCT/TH2017/000028
§ 371 (c)(1),
(2) Date: Sep. 28, 2018

(87) PCT Pub. No.: WO2017/171665
PCT Pub. Date: Oct. 5, 2017

(65) Prior Publication Data
US 2019/0106375 A1 Apr. 11, 2019

(30) Foreign Application Priority Data

Mar. 29, 2016 (TH) .............................. 1601001806 A

(51) Int. Cl.
| | | |
|---|---|---|
| *C07C 69/40* | (2006.01) | |
| *C09D 133/08* | (2006.01) | |
| *C07C 69/42* | (2006.01) | |
| *C07C 69/48* | (2006.01) | |
| *C07C 69/50* | (2006.01) | |
| *C07C 69/34* | (2006.01) | |
| *C07C 69/46* | (2006.01) | |
| *C07C 69/44* | (2006.01) | |
| *C08K 5/11* | (2006.01) | |

(52) U.S. Cl.
CPC .............. *C07C 69/40* (2013.01); *C07C 69/34* (2013.01); *C07C 69/42* (2013.01); *C07C 69/44* (2013.01); *C07C 69/46* (2013.01); *C07C 69/48* (2013.01); *C07C 69/50* (2013.01); *C09D 133/08* (2013.01); *C08K 5/11* (2013.01)

(58) Field of Classification Search
CPC ......... C07C 69/34; C07C 69/40; C07C 69/42; C07C 69/44; C07C 69/46; C07C 69/48; C07C 69/50
USPC ....................................................... 524/310
See application file for complete search history.

(56) References Cited

U.S. PATENT DOCUMENTS

| | | | | |
|---|---|---|---|---|
| 2,993,860 A | * | 7/1961 | Critchley | ................ C08F 18/08 508/344 |
| 3,347,791 A | * | 10/1967 | Davis | ........................ C10M 3/00 508/203 |
| 3,399,158 A | | 8/1968 | Jackson | |
| 5,340,487 A | * | 8/1994 | Emert | .................... C10L 1/2493 508/223 |
| 5,872,287 A | * | 2/1999 | Takaki | ..................... C07C 69/40 562/574 |
| 2009/0194003 A1 | | 8/2009 | Zhou et al. | |
| 2009/0198002 A1 | * | 8/2009 | Zhou | ........................ C09D 7/47 524/308 |
| 2012/0095145 A1 | * | 4/2012 | Zhou | ........................ C09D 7/47 524/314 |
| 2012/0258249 A1 | * | 10/2012 | Adamson | .............. C07C 69/716 427/385.5 |
| 2012/0259049 A1 | * | 10/2012 | Donate | ..................... C09D 7/20 524/290 |
| 2012/0283161 A1 | * | 11/2012 | Jung | .................... C10M 105/38 508/496 |
| 2014/0069299 A1 | * | 3/2014 | Becker | ..................... C07C 69/40 106/505 |
| 2014/0147395 A1 | | 5/2014 | Rieth et al. | |
| 2014/0243446 A1 | | 8/2014 | Turk et al. | |

FOREIGN PATENT DOCUMENTS

| | | | | | |
|---|---|---|---|---|---|
| JP | 2014043418 A | * | 3/2014 | ............. | C07C 67/00 |
| RO | 122453 B1 | * | 6/2009 | ............. | C07C 69/67 |

OTHER PUBLICATIONS

International Search Report, corresponding to PCT/TH2017/000028, dated Oct. 25, 2017.
Written Opinion of the International Searching Authority, corresponding to PCT/TH2017/000028, dated Oct. 25, 2017.

* cited by examiner

*Primary Examiner* — Jane L Stanley
(74) *Attorney, Agent, or Firm* — Renner, Otto, Boisselle & Sklar, LLP

(57) ABSTRACT

The present invention relates to a coalescing agent and a coating composition containing the coalescing agent as represented in structure (I);

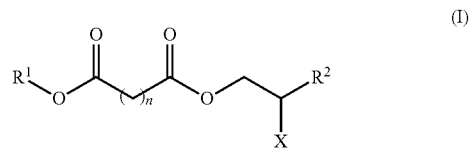

wherein; n is integer from 1 to 8; $R^1$ and $R^2$ independently represents group selected from alkyl, alkenyl, alkynyl, phenyl, or benzyl groups; and X represents group selected from hydroxy or amine. The coalescing agent according to this invention contains low amount of volatile organic compounds, has no pungent odour, and environmental friendly. Moreover, it provides good efficacy when being used as coating component.

16 Claims, No Drawings

COALESCING AGENT DERIVED FROM SUCCINATE ESTER

This application is a national phase of International Application No. PCT/TH2017/000028, filed Mar. 29, 2017, and published in the English language; which claims priority to Thailand Patent Application No. 1601001806, filed Mar. 29, 2016.

TECHNICAL FILED OF THE INVENTION

The present invention relates to a coalescing agent and a coating composition containing the coalescing agent.

BACKGROUND OF THE INVENTION

Coating agent is used for decorating the workpiece including protection of corrosion of metal workpiece, wherein such coating agent has been applied in many industries such as vehicle industry, interior and exterior construction, and also coating of many other workpiece industries.

However, from concerns in environmental problem, health including regulations issued on volatile organic compounds (VOCs), there have been many attempts in research and development in order to reduce volatile organic compounds in coating agent by substituting organic solvent composition into aqueous or high solid formulation composition.

One important composition of aqueous coating agent is the coalescing agent which is a highly volatile organic compound that helps small polymeric particle dispersed as latex in water to be adhered into thin film by reducing minimum film forming temperature (MFFT) of latex. After film had formed, the coalescing agent will move up to the surface and leave from the surface by evaporating. Therefore, the development of low VOC coalescing agent with its good properties is very necessary.

The aqueous coating agent used at present has composition of the coalescing agent about 0.1-10%, which mostly are alcohol ester, ether alcohol, or ester ketone compounds, in which said compounds are disadvantage in their pungent odour. Therefore, there have been many attempts to invent the low VOC coalescing agent with no pungent odour and is environmental friendly.

U.S. Pat. No. 4,265,797 disclosed the use of short chain monoalkyl ether of ethylene glycol or propylene glycol such as propylene glycol methyl ether as the coalescing agent.

U.S. Pat. Nos. 3,700,726 and 3,580,876 disclosed the use of ethylene glycol monobutyl ether acetate, in the name of butyl Cellosolve® as the coalescing agent and U.S. Pat. No. 3,312,652 disclosed the use of 2,2,4-trimethylpentanediol-1,3-monoisobutyrate, in the name of Texanol® as the coalescing agent.

Moreover, there were disclosures of the used of ester compounds as the coalescing agent for coating agent. For example, U.S. Pat. No. 3,399,158 disclosed the synthesis of diester derived from carboxylic acid having 2 to 6 carbon atoms such as dimethyl succinate, diethyl succinate, and diisopropyl succinate obtained from a reaction between carboxylic acid and alcohol in order to apply as the coalescing agent; US 20140243446 A1 disclosed the synthesis of diester derivative as the coalescing agent from natural precursor such as corn, cassava, lignocellulose by using organic acid obtained from biological process of said precursors to be reacted with alcohol; and the use of monoester, diester compound including blend of ester as the coalescing agent were also disclosed in patent documents and publications U.S. Pat. No. 8,586,777, WO 2009099948 A2, EP 0026982 A1, U.S. Pat. No. 7,695,557, and EP 0026982 A1.

However, there is still needs for the coalescing agent with better properties than disclosed in previous literatures. Therefore, the present invention aims to disclose the coalescing agent that has never been disclosed before, including the composition of aqueous coating agent containing the coalescing agent which is effective for the formation of film with smoothness, tolerance to hydrolysis reaction, no pungent odour, and high efficacy for work even being used in small amount.

SUMMARY OF THE INVENTION

The present invention relates to a coalescing agent as represented in structure (I);

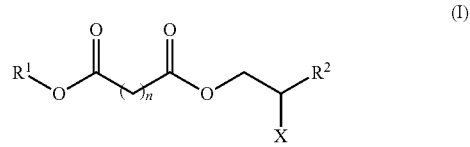

wherein;

n is integer from 1 to 8;

$R^1$ and $R^2$ are independently selected from alkyl, alkenyl, alkynyl, phenyl, or benzyl groups; and X is selected from hydroxy or amine.

In suitable form, the said coalescing agent is prepared from the reaction between diacid compound and monoalcohol compound and dialcohol compound.

In another embodiment, this invention relates to coating composition comprising:

a) at least one coalescing agent as represented in structure (I) above;

b) binder; and c) solvent

Wherein embodiment and preferable form of the coalescing agent in a) are as described above.

DESCRIPTION OF THE INVENTION

The present invention relates to the coalescing agent and the coating composition containing said coalescing agent which will be described according to the following embodiments.

Therefore, any embodiment shown here means including its application to other embodiments of this invention unless stated otherwise.

Definitions

Technical terms or scientific terms used herein have definitions which will be understood by ordinary person skilled in the art unless stated otherwise.

Any instruments, apparatus, methods, or chemicals named herein mean instruments, apparatus, methods, or chemicals being used generally by person skilled in the art unless stated otherwise that they are instruments, apparatus, methods, or chemicals specific only in this invention.

Use of singular nouns or singular pronouns with "comprising" in claims or specification means "one" and including "one or more", "at least one", and "one or more than one".

All compositions and/or methods disclosed and claimed in this application are intended to cover embodiments from any operation, performance, modification, or adjustment any factors without any experiment that significantly different from this invention, and obtain with object with utility and resulted as same as the present embodiment according to person ordinary skilled in the art although without specifically stated in claims. Therefore, substitutable or similar object to the present embodiment, including any minor modification or adjustment that can be apparent to person skilled in the art should be construed as remains in spirit, scope, and concept of invention as appeared in appended claims.

Throughout this application, term "about" means any number that appeared or expressed herein that could be varied or deviated from any error of instruments, apparatus, method, or personal using said instruments, apparatus or method.

Hereafter, invention embodiments are shown without any purpose to limit any scope of the invention.

This invention relates to the coalescing agent as represented in structure (I);

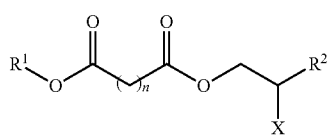

wherein;
n is integer from 1 to 8;
$R^1$ and $R^2$ are independently selected from alkyl, alkenyl, alkynyl, phenyl, or benzyl groups; and
X is selected from hydroxy or amine.

Preferable, n is integer from 1 to 4. Most preferable, n is integer of 2.

Preferable, $R^1$ and $R^2$ are independently selected from linear alkyl group having 1 to 4 carbon atoms. More preferable, $R^1$ is ethyl group and $R^2$ is methyl group.

Preferable, x is hydroxy group.

In one embodiment, the coalescing agent according to structure (I) is prepared from reaction between diacid compound and monoalcohol compound and dialcohol compound.

Said diacid compound may be selected from malonic acid, malonic anhydride, succinic acid, succinic anhydride, glutaric acid, glutaric anhydride, adipic acid, adipic anhydride, pimelic acid, pimelic anhydride, suberic acid, suberic anhydride, azelaic acid, azelaic anhydride, sebacic acid, sebacic anhydride, or mixture thereof.

Preferable, the diacid compound may be selected from malonic acid, malonic anhydride, succinic acid, succinic anhydride, glutaric acid, glutaric anhydride, adipic acid, adipic anhydride, or mixture thereof. Most preferable, the diacid compound is selected from succinic acid, succinic anhydride, or mixture thereof.

In one embodiment, the monoalcohol compound may be selected from methanol, ethanol, 1-propanol, 2-propanol, 1-butanol, 2-butanol, isobutanol, tert-butanol, or mixture thereof.

Preferable, the monoalcohol compound is ethanol.

In one embodiment, the dialcohol compound may be selected from propylene glycol, 1,2-butanediol, 1,2-pentanediol, 1,2-hexanediol, 1,2-heptanediol, 1,2-octanediol, or mixture thereof.

Preferable, the dialcohol compound is propylene glycol.

In suitable embodiment according to the invention, when n is 2, $R^1$ is selected from ethyl group, $R^2$ is selected from methyl group, and X is selected from hydroxy group, the coalescing agent according to this invention is ethyl 2-hydroxypropyl succinate according to structure (II)

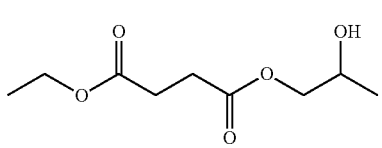

Another objective of this invention is the coating composition, comprising:
a) at least one coalescing agent as represented in structure (I);

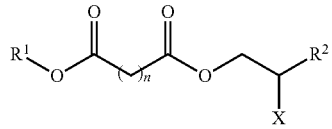

wherein;
n is integer from 1 to 8;
$R^1$ and $R^2$ are independently selected from alkyl, alkenyl, alkynyl, phenyl, or benzyl groups; and
X is selected from hydroxy or amine
b) binder; and
c) solvent.

The embodiments and the preferable embodiments of the coalescing agent in a) are as described previously.

In one embodiment, the amount of coalescing agent in a) is in the range from 1 to 20% by weight, preferable is 3 to 8% by weight.

The binder in b) may be selected from alkyd, acrylic, vinyl-acrylic, vinyl acetate/ethylene, polyurethane, epoxy, styrenic, styrenic-acrylic copolymer, styrene alkene copolymer, derivatives thereof, or mixture thereof.

Preferable, said binder is selected from acrylic, styrenic-acrylic copolymer, or mixture thereof.

In one embodiment, the amount of binder is in the range from 10 to 80% by weight, preferable is 45 to 75% by weight.

In one embodiment, the solvent in b) may be selected from solvent compatible with the coalescing agent, wherein said solvent may be selected from water, alcohol, petroleum distillate, ester, glycol, glycol ether, or mixture thereof.

In one optional embodiment, the coating composition may further comprising of pigment, pigment extender, colorant, surfactant, rheology modifier, texturing agent, defoamer, biocide, wetting agent, dispersing agent, crosslinker, thickener, antifreezing agent, stabilizer, or mixture thereof.

Also in one optional embodiment, the coating composition may further comprising of additional coalescing agent, wherein the additional coalescing agent may be selected from benzoate ester, ester-alcohol, glycol-ether, long chain aliphatic alcohol, aromatic alcohol, or mixture thereof.

The following is example which is only one embodiment of this invention and not intended to be limitation of this invention in any way.

The Preparation of Diester Derivative to be Used as the Coalescing Agent

The diester derivative which is used as the coalescing agent for the coating agent formulation can be prepared according to the following process.

The Preparation of the Coalescing Agent Ethyl 2-Hydroxypropyl Succinate (COA-1)

In the preparation of the coalescing agent COA-1, 1.0 mole succinic anhydride and 5.0 moles ethanol were added into round bottom flask and refluxed at 80° C. for 24 hours. Then, the excess ethanol of the reaction was distilled out and obtained product was extracted with the mixed solvent comprising dichloromethane and water. Then, dichloromethane layer was evaporated to obtain monoethyl succinate of the further reactions.

One mole monoethyl succinate obtained from the first step and 1.2 moles propylene glycol were added into round bottom flask and refluxed at 110° C. for 12 hours by using p-toluene sulfonic acid (1% by weight of succinic anhydride) as a catalyst. Then, solvent was evaporated from the system and extracted with dichloromethane. Sodium hydrogen carbonate was added into the product after extraction. Then, dichloromethane layer was evaporated to obtain COA-1 product which was further analyzed for its characteristics.

The Preparation of the Coalescing Agent Ethyl 2-Hydroxypropyl Succinate (COA-2)

The preparation of the coalescing agent COA-2 can be prepared by the same process as for the preparation of COA-1 but isopropanol was used instead of ethanol as alcohol in the first step.

The Preparation of the Coalescing Agent Ethyl Methyl Succinate (COA-3)

In the preparation of the coalescing agent COA-3, 1.0 mole succinic anhydride and 5.0 moles ethanol were added into round bottom flask and refluxed at 80° C. for 24 hours. Then, the excess ethanol of the reaction was distilled out and the obtained product was extracted with the mixed solvent comprising dichloromethane and water. Then, dichloromethane layer was evaporated to obtain monoethyl succinate of the further reactions.

One mole monoethyl succinate obtained from the first step and 5.0 moles methanol were added into round bottom flask and refluxed at 110° C. for 12 hours by using p-toluene sulfonic acid (1% by weight of succinic anhydride) as catalyst. Then, residual precursors from the reaction and solvent were evaporated and extracted with dichloromethane. Sodium hydrogen carbonate was added into the product after extraction. Then, dichloromethane layer was evaporated to obtain COA-3 product which was further analyzed for its characteristics.

The Preparation of the Coalescing Agent Dimethyl Succinate (COA-4)

In the preparation of the coalescing agent COA-4, 1.0 mole succinic anhydride and 6.0 moles ethanol were added in to round bottom flask with a solvent of toluene. Then, the mixture was refluxed at 110° C. for 24 hours by using p-toluene sulfonic acid (1% by weight of succinic anhydride) as catalyst. Then, residual precursors from the reaction and solvent were evaporated and extracted with dichloromethane. Sodium hydrogen carbonate was added into the product after extraction. Then, dichloromethane layer was evaporated to obtain COA-4 product which was further analyzed for its characteristics.

The Preparation of the Coalescing Agent Dibutyl Succinate (COA-5)

The preparation of the coalescing agent COA-5 can be prepared by the same process as for the preparation of COA-4 but isopropanol was used instead of butanol as alcohol in the first step.

Properties Testing of Diester Derivatives

The said obtained diester derivatives were analyzed by the following methods.

Film Forming Efficacy

The film forming efficacy of the coalescing agent COA-1 to COA-5 comparing to the commercial coalescing agent Texanol™ and Butyl Cellosolve™ can be performed according to the following steps.

1. 20 g of binders (acrylic or copolymer of styrenic-acrylic) were added into testing beaker.

2. 1-15% by weight of the tested coalescing agent from COA-1 to COA-5 was slowly added during stirred until the coalescing agent was homogeneously mixed with the binder. This took about 10-15 mins in order to complete the each concentration of 1-15% of coalescing agent that had been prepared.

3. The prepared coalescing agent and the binder obtained from 2 were drawn onto supporting paper using wire coater until 100 micron thick film layer was obtained. Then, the obtained film was left to be dried at room temperature.

4. When the film was dry, appearance of film was observed. The film must be transparent and not broken. Then, percentage of the coalescing agent capable to produce good film was recorded.

Drying Property

The drying property of the coalescing agent COA-1 to COA-5 comparing to the commercial coalescing agent Texanol™ and Butyl Cellosolve™ can be performed according to the following steps.

1. 20 g of binder selected from acrylic or copolymer of styrenic-acrylic and the amount of the coalescing agent COA-1 to COA-5 capable to produce the best film were added into testing beaker. The mixture was mixed and stirred until homogeneously mixed.

2. The prepared coalescing agent and binder obtained from 1 were drawn onto supporting paper using wire coater until 100 micron thick film layer was obtained. Then, the obtained film was left to be dried at room temperature.

3. The prepared film was touch by finger. The time that there was no fingerprint shown on the film was recorded.

Odour Testing

The odour testing of the coalescing agent COA-1 to COA-5 comparing to the commercial coalescing agent Texanol™ and Butyl Cellosolve™ can be performed according to the following steps.

1. 10 g of the coalescing agent COA-1 to COA-5 were added into each testing beaker.

2. Five assessors were asked to smell and recorded the odour intensity from 0-3, wherein 3 meant highest odour intensity and 0 meant no odour detected.

Volatile Organic Compound (VOC) Testing

The testing of VOC of the coalescing agent COA-1 to COA-5 comparing to the commercial coalescing agent Texanol™ and Butyl Cellosolve™ can be performed according to the ISO 11890-2 standard.

The Properties of the Coalescing Agent

The properties of the coalescing agent COA-1 to COA-5 comparing to the commercial coalescing agent Texanol™ and Butyl Cellosolve™ is shown in table 1. From the tests, it can be seen that the coalescing agent COA-1 and COA-2 according to the present invention has the same level of the film forming efficacy as those commercial coalescing agents. These coalescing agents according to the present invention need only 6% by weight in order to produce film as same as those commercial coalescing agents. On the other hand, the rest of coalescing agents, which are alkyl succinate esters of COA-3, COA-4, and COA-5, are not able to form polymer film of binders. Moreover, the coalescing agent according to the present invention need similar drying time as those commercial coalescing agents. The coalescing agent according to the present invention has less odour intensity than those commercial coalescing agents. This shows that the coalescing agent according to the present invention has similar efficacy as those commercial coalescing agents but has less odour intensity and lower amount of volatile organic compound.

TABLE 1

Properties of the coalescing agent according to the present invention comparing to the commercial coalescing agents

| | Acrylic Binder | | | | Copolymer of Styrenic-Acrylic Binder | | | | |
| --- | --- | --- | --- | --- | --- | --- | --- | --- | --- |
| Sample | Amount used to form film (% by weight) | Film characteristic | Drying of film (min) | Odour | Amount used to form film (% by weight) | Film characteristic | Drying of film (min) | Odour | VOC (g/l) |
| Texanol ™ | 5 | transparent | 28 | 3 | 5 | transparent | 20 | 3 | 4.48 |
| Butyl Cellosolve ™ | 9 | transparent | 25 | 3 | 6 | transparent | 20 | 3 | 4.98 |
| COA-1 | 6 | transparent | 27 | 1 | 5 | transparent | 20 | 1 | 1.27 |
| COA-2 | 6 | transparent | 26.5 | 1 | 6 | transparent | 20 | 1 | 1.25 |
| COA-3 | film cannot be formed | — | — | — | film cannot be formed | — | — | — | — |
| COA-4 | film cannot be formed | — | — | — | film cannot be formed | — | — | — | — |
| COA-5 | film cannot be formed | — | — | — | film cannot be formed | — | — | — | — |

BEST MODE OR PREFERRED EMBODIMENT OF THE INVENTION

Best mode or preferred embodiment of the invention is as provided in the description of the invention.

The invention claimed is:

1. A coalescing agent as represented in structure (I);

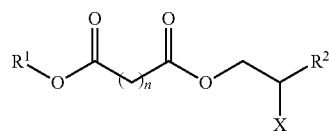

(I)

wherein;
n is integer from 1 to 8;
$R^1$ and $R^2$ are independently selected from alkyl, alkenyl, alkynyl, phenyl, or benzyl groups; and
X is selected from hydroxy or amine.

2. The coalescing agent according to claim 1, wherein n is integer from 1 to 4.

3. The coalescing agent according to claim 1, wherein $R^1$ and $R^2$ are independently selected from linear alkyl group having 1 to 4 carbon atoms.

4. The coalescing agent according to claim 1, wherein X is hydroxy group.

5. The coalescing agent according to claim 1, wherein said coalescing agent is prepared from a reaction between a diacid compound selected from malonic acid, malonic anhydride, succinic acid, succinic anhydride, glutaric acid, glutaric anhydride, adipic acid, adipic anhydride, or mixtures thereof; a monoalcohol compound selected from methanol, ethanol, 1-propanol, 2-propanol, 1-butanol, 2-butanol, isobutanol, tert-butanol, or mixtures thereof; and a dialcohol compound selected from propylene glycol, 1,2-butanediol, 1,2-pentanediol, 1,2-hexanediol, 1,2-heptanediol, 1,2-octanediol, or mixtures thereof.

6. The coalescing agent according to claim 1, wherein the coalescing agent is ethyl 2-hydroxypropyl succinate.

7. A coating composition, comprising:
a) at least one coalescing agent as represented in structure (I);

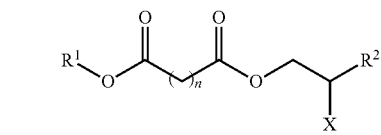

(I)

wherein;
n is integer from 1 to 8;
$R^1$ and $R^2$ are independently selected from alkyl, alkenyl, alkynyl, phenyl, or benzyl groups; and
X is selected from hydroxy or amine
b) binder; and
c) solvent.

8. The coating composition according to claim 7, wherein n is integer from 1 to 4.

9. The coating composition according to claim 7, wherein $R^1$ and $R^2$ are independently selected from linear alkyl group with 1 to 4 carbon atoms.

10. The coating composition according to claim 7, wherein X is hydroxy group.

11. The coating composition according to claim 7, wherein said coalescing agent is prepared from a reaction between a diacid compound selected from malonic acid, malonic anhydride, succinic acid, succinic anhydride, glutaric acid, glutaric anhydride, adipic acid, adipic anhydride, or mixtures thereof; a monoalcohol compound selected from methanol, ethanol, 1-propanol, 2-propanol, 1-butanol, 2-butanol, isobutanol, tert-butanol, or mixtures thereof; and a dialcohol compound selected from propylene glycol, 1,2-butanediol, 1,2-pentanediol, 1,2-hexanediol, 1,2-heptanediol, 1,2-octanediol, or mixtures thereof.

12. The coating composition according to claim 7, wherein the coalescing agent is ethyl 2-hydroxypropyl succinate.

13. The coating composition according to claim 7, wherein the amount of coalescing agent is in the range from 3 to 8% by weight and wherein the amount of binder is in the range from 45 to 75% by weight.

14. The coating composition according to claim 7, wherein said binder is selected from alkyd, acrylic, vinyl-acrylic, vinyl acetate/ethylene, polyurethane, epoxy, styrenic, styrenic-acrylic copolymer, styrene alkene copolymer groups, derivatives thereof, or mixtures thereof.

15. The coating composition according to claim 7, wherein said solvent is selected from water, alcohol, petroleum distillate, ester, glycol, glycol ether, or mixtures thereof.

16. The coating composition according to claim 7, wherein the coating composition further comprises an additive selected from pigment, pigment extender, colorant, surfactant, rheology modifier, texturing agent, defoamer, biocide, wetting agent, dispersing agent, crosslinker, thickener, antifreezing agent, stabilizer, or mixtures thereof.

\* \* \* \* \*